United States Patent [19]

Frossard

[11] Patent Number: 4,801,531
[45] Date of Patent: Jan. 31, 1989

[54] APO AI/CIII GENOMIC POLYMORPHISMS PREDICTIVE OF ATHEROSCLEROSIS

[75] Inventor: Philippe M. Frossard, Palo Alto, Calif.

[73] Assignee: Biotechnology Research Partners, Ltd., Mountain View, Calif.

[21] Appl. No.: 782,666

[22] Filed: Sep. 30, 1985

Related U.S. Application Data

[63] Continuation-in-part of Ser. No. 724,192, Apr. 17, 1985, abandoned.

[51] Int. Cl.[4] ...................... C12Q 1/68; G01N 33/567
[52] U.S. Cl. ......................................... 435/6; 435/810; 436/63; 436/14; 436/503; 536/27; 935/11; 935/78; 935/79
[58] Field of Search ...................... 435/6, 810; 436/63, 436/94, 501, 503; 536/27; 935/11, 78, 79

[56] References Cited

U.S. PATENT DOCUMENTS

4,623,619 11/1986 Owerbach et al. ............. 436/811 X

OTHER PUBLICATIONS

Rees et al., "DNA Polymorphism Adjacent to Human Apo-Protein A-1 Gene . . . ", The Lancet, Feb. 26, 1983, pp. 444-446.
Karathanasis et al., "An Inherited Polymorphism in the Human Apolipoprotein A-1 Gene . . . ", Nature 301, 718-720 (1983).
Wallis et al., "The Isolation of a Genomic Clone Containing the Apolipoprotein CII Gene . . . ", Hum. Genet 68, 286-289 (1984).
Fojo et al., "Analysis of the Apo C-II Gene . . . ", Biochem Biophys Res. Comm. 124(1), 308-313 (1984).
Seilhamer, J. J., et al., "Isolation and DNA Sequence . . . Discovery of a New Genetic Polymorphism in the Apo AI Gene", DNA 3(4), 309-317 (1984).
Antonarakis, W. E. et al., Proc. Natl. Acad. Sci. (USA) (1983) 79:137.
Gianelli et al., Lancet (1984) i:2369, 4 Feb.
Grunebaum et al., J. Clin. Invest. (1984) 73:1491.
Gusella, J. F. et al., Nature (1983) 306:234.
Jeffreys, A. J., Cell (1979) 18:1-10.
Kan, Y. W. et al., Proc. Natl. Acad. Sci. (USA) (1978) 75:5631.
Ostyer, H. et al., Am. J. Hum. Gen. (1984) 36(Supp):150S.
Phillips, J. A., III, Banbury Report 14, Cold Spring Harbor Laboratory (1983) pp. 305-315.
Rotwein, P. et al., Science (1981) 213:1117.
Southern, E., J. Mol. Biol. (1975) 98:503-517.
Woo, S.L.C. et al., Nature (1983) 306:151.

Primary Examiner—Robert J. Warden
Assistant Examiner—Richard Wagner
Attorney, Agent, or Firm—Ciotti & Murashige Irell & Manella

[57] ABSTRACT

The invention offers an early detection method for atherosclerosis using genetic analysis to detect a polymorphisms shown to be correlated with this disease which are proximal to the apolipoprotein AI (apoAI) and aplipoprotein CIII (apoCIII) gene complex. All individuals with a 300 bp deletion 4 kb upstream of the apoAI gene are destined to experience severe atherosclerotic symptomologies. Individuals with a polymorphism 5.4 kb 5' of the apoAI gene or a PvuII polymorphism in the first intron of the apoCIII gene also seem to be at greater risk. A haplotype with MspI and XmnI/7.2 polymorphisms in this general region seem to be protected. Additional polymorphic sites in the DNA sequence associated with the apoAI/CIII gene complex provide a means for genetically fingerprinting individuals, and for identifying persons at risk with respect to disorders relating to lipid metabolism and transport.

32 Claims, 4 Drawing Sheets

```
        220         230         240         250         260         270         280
AGGCAGCTGC TCCAGGTAAT GCCCCTCTGGG GAGGGGAAAG AGGAGGGGAG GAGGATGAAG AGGGGCAAGA 290         300         310         320         330         340         350
GGAGCTCCCT GCCAGCAAGC CTGGAGAAGC ACTTGCTAGA GCTAAGGAAG CCTCGCAGCT PvuII 360         370         380         390         400         410         420
GGACGGGTGC CCCCCACCCC TCATCATAAC CTGAAGAACA TGGAGGCCCG GGAGGTGTCA CTTGCCCAAA

SstI/BanII
        3132                 3145         3155         3165         3175         3185         3195
GCT GCC TGA GACCTCAATA CCCCAAGTCC ACCTGCCTAT CCATCCCTGCG AGCTCCTTGG GTCCTGCAAT
Ala Ala 3205         3215         3225         3235         3245         3255         3265
CTCCAGGGCT TCCCCTGTAG GTTGCTTAAA AGGGACAGTA TTCTCAGTGC TCTCCTACCC CACCTCATGC

MspI                               BanII
        6310         6320         6330         6340         6350         6360         6370
CAGATGCGTGC GCGCAGCGCG CGTCCACACATG GGCGCGCGCG CGTCGCGCCA CATCTCCTCG CCCCAGTGGGCTCAGC 7080         7090         7100         7110         7120         7130         7140
TTTGCAGGGA CATGGGCTGT GACCCTGCCT GGAGATCCATT CCGGTTTCTC CATCCAGACC ACCCCCTGG
```

FIG.5

APO AI/CIII GENOMIC POLYMORPHISMS PREDICTIVE OF ATHEROSCLEROSIS

CROSS-REFERENCE TO RELATED APPLICATION

This is a continuation-in-part of U.S. Ser. No. 724,192, filed 17 Apr. 1985 now abandoned.

TECHNICAL FIELD

The invention relates to the use of genetic polymorphisms to determine disease states. More particularly, the invention concerns the use of polymorphisms of the apolipoprotein AI/CIII gene complex to diagnose susceptibilities to atherosclerosis.

BACKGROUND ART

The degree of morbidity and mortality associated with atherosclerosis in developed countries is higher than that associated with any other particular disorder, even cancer. The disorder manifests itself in the form of cholesterol deposition in arterial cell walls. The deposition is slow and irreversible and starts at an early age. Clinical symptoms may take years to manifest themselves and are extremely serious; they include coronary heart disease and stroke. Generally, the disease process will have begun long before these clinical manifestations appear.

Because environmental as well as hereditary factors influence the course of the cholesterol deposition and offer means for at least a mitigation of the process, it is desirable to have available a diagnostic technique which provides an early warning of the onset of the deposition. The present technique depends on measuring cholesterol or triglyceride levels in serum, and while these levels are, indeed, capable of accurate measurement, they do not offer the desirable high correlation to true susceptibility. More reliable predictive methods, which rely on detection of atheromatous lesions, use highly invasive procedures, which are sufficiently painful and expensive that they cannot be employed on a screening basis, or even applied to specific groups selected on the basis of family histories. These techniques also offer too little, too late; by the time the atheromatous lesions have appeared, the most effective time for treatment has been passed.

The importance of early detection is made more poignantly evident by the fact that an effective, but inconvenient and unattractive long term treatment is available---i.e., lowering serum cholesterol through consistently controlled diet or use of cholesterol-lowering drugs. Resistance to this approach will be encountered unless it is clear that the "deprivation" is warranted. The problem is not what the treatment should be, but to whom the treatment should be applied.

A technique that inherently offers the advantages of early detection, if its results can be effectively correlated with the disorder to be assessed, is genetic analysis. Since the genomic characteristics of an individual are basically determined, it is assumed, at conception, genetic aberrations which are indicia of later metabolic disorders are an ideal early diagnosis tool. Genetic testing can be routinely conducted using present methodology, as early as the seventh week of fetal life. Over the last ten years, the availability of restriction enzymes and DNA probing techniques has made possible the use of "restriction fragment length polymorphisms" (RFLPs) in such diagnosis. Using the, by now, well established Southern blot hybridization technique (Southern, E., *J Mol Biol* (1975) 98:503–517), it has been possible successfully to diagnose sickle cell anemia (Kan, Y.W., et al, *Proc Natl Acad Sci (USA)* (1978) 75:5631); β-thalassemia (Antonarakis, S.E., et al, *Proc Natl Acad Sci (USA)* (1983) 79:137); type II diabetes (Rotwein, P., et al, *Science* (1981) 213:1117); familial growth hormone deficiency (Phillips, J.A., III, *Banbury Report* 14, Cold Spring Harbor Laboratory (1983) pp 305–315); phenylketonuria (Woo, S.L.C., et al, *Nature* (1983) 306:151); Huntington's disease (Gusella, J.F., et al, *Nature* (1983) 306:234); and hemophilia B (Gianelli, et al, *Lancet* (1984) i:239, Grunenbaum, et al, *J Clin Invest* (1984) 73:1491).

All of the foregoing successes are grounded in identification of a particular polymorphism or polymorphisms which correlates with the disease or disorder in question. It has been calculated that the number of polymorphisms expected in the human genome should be of the order of $10^7$, based on an assumed probability of 0.05 for a given nucleotide to be polymorphic; this number being inferred from studies of the human growth hormone, αI-antitrypsin and β-like globin gene cluster loci (Jeffreys, A. J., *Cell* (1979) 18:1–10; Oster, H., et al, *Am J Hum Gen* (1984) 36(suppl) 150S). The challenge is to determine which of these over ten million polymorphisms is associated with a particular disorder, and to devise a procedure to detect it. The present invention has met this challenge with regard to atherosclerosis, and has also identified a pattern of polymorphisms associated with the same location in the genome useful in characterizing particular individuals and patterns of inheritance.

DISCLOSURE OF THE INVENTION

The invention provides identification of polymorphisms which are highly predictive of the subsequent development of atherosclerosis and others which are indicative of an individual protected against development of this disease. Additional polymorphisms have also been found in this region of the genome which encodes apolipoproteins AI and CIII (the apoAI/CIII region). These polymorphisms, taken together or in subsets, can provide an identity profile of a particular individual, thus providing a means to follow family inheritance patterns and to assess relationship between individuals. In addition, since these polymorphisms are located in the genomic sequences which regulate lipid metabolism, it is probable that their pattern of presence or absence will show some additional specific, as yet unknown, correlation to symptomology.

Thus, in one aspect, the invention is directed to a method of predicting the likelihood of development of atherosclerosis in an individual, which method comprises:

detecting the presence or absence of deletion of approximately 300 bp of DNA at about 4 kb 5' of the apolipoprotein AI (apoAI) gene (the "XmnI/8.2" polymorphism); and/or detecting the presence of absence of a polymorphism 5.4 kb 5' of the apoAI gene (The "ApaI" polymorphism); and/or detecting the presence of absence of a polymorphism in the first intron of the apoCIII gene (the "PvuII" polymorphism); and/or detecting the presence or absence of polymorphisms 3.7 kb 5' of the apoAI gene (the "XmnI/7.2" polymorphism) and in the third intron of the apoAI gene (the "MspI" polymorphism).

Stated alternatively, the invention is directed to a method for detecting susceptibility to atherosclerosis which comprises:

detecting presence or absence of an 8.2 kb XmnI digestion fragment hybridizing to apoAI or p5'AI probes, or their substantial equivalents; and/or detecting the presence or absence of a 2.2 kb ApaI digestion fragment hybridizing to a p5'AI probe or its substantial equivalent; and/or detecting the presence or absence of a 0.87 PvuII digestion fragment hybridizing to an apoCIII probe or its substantial equivalent, and/or detecting the presence or absence of a 7.2 kb XmnI fragment and a 1.75 kb MspI fragment hybridizing to an ApoAI probe or its substantial equivalent.

In still another aspect, the invention relates to determination of a genetic fingerprint of a subject which relates to disorders of lipid metabolism and transport using polymorphisms of the apoAI/CIII gene region. The invention is also directed to kits suitable for performing the methods of the invention.

MODES OF CARRYING OUT THE INVENTION

In the description below, distances of polymorphisms from reference points and lengths of deletions are often given in bp or kb. Where the sequence is known, such measures can be quite precise, but when assessed by measuring fragment sizes on gels or by other experimental means, these measures contain a margin of uncertainty, as is well understood in the art. In general, for measures of >4 kb, the margin of uncertainty is ±∼0.3 kb; for smaller lengths, the error is ±∼10%. Thus, the "300 bp" deletion may be slightly larger or smaller, and the 4 kb spacing from the apoAI gene is only approximate.

A. Techniques for Detection of Polymorphisms

Application of the method of the invention to predict potential atherosclerotic individuals or to obtain a genetic "fingerprint" based on some or all of the nine polymorphisms associated with the general genomic apoAI/CIII region, employs standard techniques of DNA extraction, purification, restriction enzyme digestion, and size separation. Techniques for hybridization with probe and detecting successfully hybridized substrate arranged according to molecular weight are also well known to those in the art. The general approach to finding and detecting the significant polymorphisms is the following:

DNA is extracted from the somatic cells of the individual to be tested, for example from leukocytes, placental cells, cultured fibroblasts, or, in the case of fetal individuals, from cells of the amniotic fluid. The high molecular weight DNA fraction is separated, and subjected to treatment with a particular, selected restriction enzyme, such as, for example, EcoRI, BamHI, MstI, XmnI, and the like. After digestion of the high molecular weight DNA, the digest is applied to a polyacrylamide or agarose gel and subjected to electrophoresis to obtain separation of the DNA fragments resulting from restriction enzyme digestion into positions on the gel determined by the size (length) of the fragment. The contents of the gel are then replicated by transferring to a nitrocellulose filter or other suitable matrix for use as a probe hybridization support. The DNA fragments, either before or after transfer to the nitrocellulose filter replica, are treated with a denaturant such as sodium hydroxide/salt. The denatured, single-stranded DNA, replicated electrophoresis patterns are probed with labeled (usually by $^{32}$P) single-stranded DNA fragments. Other labels besides radioactivity, such as fluorescent molecules may also be used.

Depending on the probe selected, fragments will be detected which derive from a particular region on the genome. For example, in the method of the invention, a cDNA sequence from the apolipoprotein AI (apoAI) or apolipoprotein CIII (apoCIII) gene sequences is used as a probe. Therefore, the only fragments which will appear on the hybridized filters are those which contain sequences complementary to this probe—i.e., only those which have not been severed either in the genome itself or by the restriction enzyme cleavage from the complementary apoAI or apoCIII fragment. Stated in another way, by using a particular probe, alterations in the genome which are proximal to sequences corresponding to that probe area detected.

The specific procedures used in the general process described in the preceding paragraphs are understood in the art. Procedures for DNA extraction from somatic cells may, for example, be found in Kan, Y.W., et al, *Proc Natl Acad Sci* (USA) (1978) 75:5631–5635; Taylor, J.M., et al, *Nature* (1984) 251:392–393; and Kan, U.W., et al, *N Eng J Med* (1977) 297:1080–1084. Further improvements which permit rapid extraction of the DNA are also disclosed by Law, D. G., et al, *Gene* (1984) 28:153–158. Techniques for size separation of the restriction enzyme treated DNA fragments are also described in the foregoing references. Restriction enzyme digestions are generally standard in the art and are carried out under buffer, ionic strength, and temperature conditions which are specified by the manufacturer of the particular restriction enzyme.

Transfer to nitrocellulose or other support and probing by prehybridization with nonspecific DNA followed by hybridization with labeled probe are also standard procedures disclosed, for example, in the foregoing references and by Southern, E., (supra). The section of the genome which is fingerprinted or otherwise subject to study using the results is, of course, dependent on the nature of the probe. The probes useful in the present invention are selected from the apoAI/-CIII gene complex.

B. Nature of the Probes Useful in the Invention

The fragment pattern obtained is diagnostic for a particular polymorphism if the probe selected is complementary to a DNA sequence sufficiently proximal to the polymorphism on the genome that it is not severed from the polymorphism by the restriction cleavage, and has a low probability of being segregated from the polymorphism by crossing over. Acceptable distance limits between the region of probe complementarity and the polymorphism are therefore arbitrary. Generally, probes which hybridize to DNA sequences within 10 kb upstream or downstream of the polymorphism give acceptable results. Occasionally, the pattern of restriction enzyme cleavage may place a distal probe hybridization site on a fragment irrelevant to the polymorphism. The closer the probe to the polymorphism, the greater the range of usable restriction enzymes. Accordingly, as used herein, a probe which is a "substantial equivalent" to a specified probe is one which hybridizes to the same fragment length in digests of DNA from individuals with a particular polymorphism when the same restriction enzyme is used. Thus, for XmnI digestion diagnosis of individuals with the 4 kb 5' deletion upstream of the apoAI gene, the apoAI and p5'AI probes (described below) are equivalent. For RsaI digestion, they are not. (Of course, the designated probe can be modified in a trivial manner by being made longer or shorter or by selecting a slightly displaced sequence.)

Since atherosclerosis is associated with a defect in cholesterol metabolism, the apoAI/apoCIII game which is associated with regulation of blood plasma cholesterol was chosen as a region of appropriate probe complementarity. Regulation of blood plasma cholesterol is related to high density lipoprotein (HDL), which is known to be a carrier of cholesterol in the bloodstream, and thus believed to play a significant role in regulating its level—apoAI is the major structural protein of HDL. It is a 243 amino acid polypeptide having a molecular weight of 28,000. In addition to being a structural member of the HDL complex, apoAI is also an activator of lecithin-cholesterol acyltransferase, which enzyme is responsible for transforming the lamellar surface structures of chylomicrons into pseudomicellar spherical HDL by de novo synthesis of cholesterol esters and lysolecithin. The apoAI protein may also be the HDL component recognized by the HDL receptors.

According, the apoAI gene region seemed a portion of the genome where modification might occur in individuals with a prognosis for atherosclerosis or related disorders. This gene lies close to a related gene encoding apolipoprotein CIII (apoCIII) which is 2.5 kb from the apoAI gene on the long arm of chromosome 11 (Cheung, P., et al, *Proc Natl Acad Sci (USA)* (1984) 81:508-511; Law, S. W., et al, *Biochem Biophys Res Commun* (1984) 118:934-942). This region of the genome is herein designated the "apoAI/CIII complex". Genomic and cDNA clones for both apoAI and apoCIII have been isolated by, e.g., Karathanasis, S. K., et al, *Proc Natl Acad Sci (USA)* (1983) 80:6147-6151; shoulders, S. C., et al, *Nucleic Acids Res* (1983) 11: 2827-2837 and by others. Various apoAI and apoCIII probes have been described (see, e.g., Karathanasis, S.K., et al (supra); Shoulders, S.C., et al (supra) and have been used previously as hybridization probes to detect polymorphisms.

Karathanasis, S. K., et al, (*Nature* (1983) 301:718-720; ibid (1983) 305:823-825) showed a 6.5 kb DNA insertion in the coding region of apoAI in one family suffering from HDL deficiency. Rees, A., et al, *Lancet* (1983) i:444-446 showed an SstI polymorphism in the 3' flanking region of the apoAI gene which was present in some hypertriglyceridemic patients. Seilhamer, J.J., et al, *DNA* (1984) 3:309-317 have disclosed an MspI polymorphism in the third intron of the apoAI gene.

The apoAI, apoCIII, and p5'AI probes which illustrate those useful in the invention are described in detail in §F.1, below. Any probes substantially equivalent to these for a specific restriction enzyme, as defined above, may be used.

The relationship of the probe/enzyme combination to results is illustrated using one atherosclerosis predictive polymorphism of the invention which consists of an approximately 300 bp deletion about 4 kb 5' of the apoAI gene (see below). The deletion is detectable, for example, by digesting the extracted cellular DNA with XmnI, subjecting the fragments to electrophoresis gel separation, and probing with either apoAI or p5'AI probes. As explained below, all persons showing an 8.2 kb fragment are at high (perhaps 100%) risk of developing atherosclerosis, if, indeed, the symptoms have not already appeared. Because of the pattern of XmnI restriction sites in this region, the apoAI and p5'AI probes are substantial equivalents in this test. Based on this pattern, one would expect that substantially equivalent probes would be found within 10 kb of the polymorphism, i.e., within about 14 kb upstream or 4 kb downstream of the apoAI gene with respect to digestion with XmnI. These two probes are, however, not equivalent with respect to a series of additional restriction enzymes which are capable of detecting this polymorphism but which cut either closer to the polymorphism or on the side of its opposite the apoAI gene. For such restriction enzymes, probes equivalent to p5'AI must be located between the restriction site and the polymorphism.

Probes are labeled by nick translation using α [$^{32}$P] dCTP and α [$^{32}$P] dGTP, which results in fragmentation of the probe. Thus, cDNA probes which are complementary only to the exon regions of the gene (shown as thickened portions of the genomic regions in FIGS. 2, 3, and 4) and which span over intron regions are workable in the method of the invention.

C. Atherosclerosis-Related Polymorphisms

C.1. The XmnI/8.2 Polymorphism

One abnormal allele associated with atherosclerosis, i.e., that containing the above-mentioned 300 bp deletion, results in an 8.2 kb XmnI digest fragment, detectable with either of apoAI or p5'AI probes, rather than the 8.5 kb fragment which is obtained "normally". The definition of "normal" in the foregoing sense has to do with the nature of the disease being diagnosed and describes a genomic makeup which does not dispose the subject to the disorder. The majority of the total population will be "normal".

To correlate the genetic test results with atherosclerosis, 125 individuals were tested using XmnI and apoAI or p5'AI probe. DNA from ten of these individuals contained the 300 bp deletion, i.e., yielded the 8.2 kb fragment. All of these ten had previously suffered a myocardial infarction; furthermore the presence of the deletion correlated with low levels of HDL cholesterol, the major feature of familial combined hyperlipidemia, a disease associated with early development of severe atherosclerosis and its subsequent clinical symptoms. Twenty-five of the individuals tested were normal control healthy individuals; the DNA from none of these persons contained the deletion. The remaining ninety tested individuals (also not showing the 8.2 kb fragment) were known the have atheromatous plaques as detected by angiography, but not all had suffered heart attacks. Thus, in this sample the deletion is present only in individuals at serious risk from atherosclerosis. It is not present in all such individuals. Therefore, a positive test using this polymorphism is diagnostic and predictive and preventive methods of therapy would be clearly appropriate. (Of course, a negative test may not mean that the individual is at no risk; it may merely indicate that other genetic defects or other factors predispose that individual to the atherosclerosis problem.)

C.2. Additional Predictive Polymorphisms

The various polymorphisms associated with the apoAI/CIII region were also analyzed using a different group of individuals from that discussed in §CL above. This group was divided into atherosclerosis "patients" i.e., those persons shown to have atheromatous plaques as detected by angiography, whether or not they had heart attacks; and "controls", which consist of those with negative results in this test. Use of this division permits statistical analysis of data to assign increased or decreased risk of atherosclerosis, depending on the presence of absence of particular polymorphisms. The ApaI, XmnI/8.2, XmnI/7.2, MspI, PstI, BanI, and PvuII polymorphisms (see Table 2 below) were tested using 550 individuals and analyzed according to these criteria. Based on the results of this analysis, individuals having the ApaI, XmnI/8.2, or PvuII polymorphisms show an increased risk of atherosclerosis; individuals having both XmnI/7.2 and MspI polymorphisms appear to be protected against the disease.

D. Additional Polymorphisms

Additional polymorphisms in the apoAI/CIII gene region were obtained and are set forth along with those discussed above in detail in Table 2 of the examples below. Some of these polymorphisms have been characterized in terms of their location; however, all can be defined operationally as detectable by digestion by a particular restriction enzyme and probing with a specific probe or its substantial equivalent. The pattern of the presence or absence of these polymorphisms is capable of fingerprinting an individual genetically so that hereditary patterns between parents and progeny can be traced. Also, because these polymorphisms are associated with a region of the genome important in lipid metabolism and transport, the presence of one or, more probably, several of these polymorphisms is likely to be associated with a propensity to disorders of lipid metabolism and related symptomologies. At the present time, limited precise correlations have been made between the presence of particular polymorphisms in this group and particular symptomologies. However, ascertaining the presence or absence of these genetic modifications is useful for the general purpose of identifying individuals with presumptively high risk of lipid disorder symptomologies and for providing a genetic characterization of individuals and family patterns.

One particular application is illustrated by the ability of the method of the invention to detect individuals with Tangier disease. Tangier disease is a rare, autosomal recessive disorder characterized by the absence of HDL from the plasma and an increase in the amount of cholesteryl esters stored in several organs. Patients are characterized clinically by tonsillar hypertrophy, splenomegaly, and transient peripheral neuropathy. See Herbert, P.N., et al (1982), in *The Metabolic Basis of Inherited Disease* (McGraw-Hill, New York), Stanbury, J.B., et al, eds. Of 125 individuals tested in the illustration below, only the three among them showing Tangier disease symptomology exhibited a characteristic haplotype based on a set of 5 polymorphisms. Therefore, this 5-polymorphism subset can be used as a predictor of the development of the disease.

E. Kits

The reagents suitable for applying the method of the invention to detect the appropriate polymorphisms may be packaged into convenient kits providing the necessary materials, packaged into suitable containers, and, optionally, suitable containers or supports useful in performing the assay. The essential components of the assay include the restriction enzyme associated with the polymorphism, and a suitable probe. Additionally, packages containing concentrated forms of reagents used for hybridization, prehybridization, DNA extraction, etc. may be included if desired. In particular, however, labeled probe, or reagents suitable to form conveniently labeled probe, are useful in facilitating the conduct of the method of the invention.

F. Examples

The following examples are specific with respect to the probes exemplified and with respect to the precise conditions of DNA extraction, probe hybridization, etc. It is understood that these factors are illustrative but not limiting. The essential features of the invention as it relates to detection of a particular polymorphism are selection of enzyme and probe. For example, in the XmnI/8.2 embodiment for atherosclerosis prediction, one may use XmnI digestion of the genomic DNA and probe with a sequence complementary to the genomic sequence (in the nonrepeating regions) proximal (i.e., within~in this case <8.2 kb) to the site of the polymorphism. Alternatively, other restriction enzymes may be used in conjunction with a probe which hybridizes in particularly close proximity to the polymorphism.

The various polymorphisms identified may be detected using other specific restriction enzymes. A variety of substantially equivalent probes could be designed with respect to this region, and the particular restriction enzyme and cDNA probe chosen are arbitrary. However, it should be noted, as is understood in the art, that the efficacy of the probe is enhanced as it moves closer to the site of the polymorphism. Otherwise, additional cleavage points may be encountered between the polymorphism and the probe, and also the probing site may be separated from the site of the polymorphism during replication by crossing-over events.

F.1. Procedures for Analysis

Leukocytes were obtained from freshly drawn blood collected from each of the human subjects, and high molecular weight genomic DNA was isolated by the procedure of Law, D. J., et al, *Gene* (1984) 28:153-158.

High molecular weight DNA was divided into portions and each was digested to completion with one of the various restriction enzymes under conditions recommended by the suppliers (New England Biolabs and Bethesda Research Laboratories). The digests were electrophoresed in horizontal agarose gels in 30 mM NaH2PO4, 36 mM Tris, 1 mM EDTA, pH 7.7. After electrophoresis, DNa fragments were denatured in situ in 0.5 M NaOH/1.5 M NaCl for 2×10 min, neutralized in 1 M ammonium acetate pH 7.2 for 2×10 min, and transferred overnight into nitrocellulose paper (Schleicher and Schuell). The filters were rinsed in 2×SSC (1x SSC is 0.15 M NaCl, 0.015 M sodium citrate pH, 7.4) and baked for 2 hr at 80° C. in vacuo and then were prehybridized for 5 hr in plastic bags using 0.3 ml/cm$^2$ of a solution containing 5x SSPE (1×SSPE is 10 mM Na phosphate pH 7.4, 0.18 M NaCl and 1 mM EDTA) containing 5×Denhardt's solution (1×Denhardt's contains 0.2 mg/ml each of Ficoll, polyvinylpyrrolidone and bovine serum albumin), 40% (vol/vol) formamide, and 250 µg/ml sheared and denatured salmon spern DNA, and hybridized overnight in the same bag in 0.1 ml/cm$^2$ of 5×SSPE, 1×Denhardt's solution, 40% (vol/vol) formamide, 10% dextran sulfate, and 100 µg/ml sheared and denatured salmon sperm DNA, mixed with 100 ng per bag (containing 1 or 2 filters) of the appropriate $^{32}$P-labeled probe, as discussed below. Prehybridization and hybridization were performed at 42° C.

Filters were then washed twice at room temperature in 2×SSC and twice at 65° C. in 2×SSC, 1x Denhardt's solution. DNA sequences hybridized to the $^{32}$P-labeled probes were visualized by autoradiography using XAR-5 films (Kodak) and Cronex intensifying screens (Dupont) at −70° C. for 18 hr to 2 days.

Three specific probes are used in the illustrations below: apoAI probe, apoCIII probe, and p5′AI probe.

The apoAI was a 600 bp cDNA fragment which had been cleaved with AvaII to remove terminal A/T tails as described by Seilhamer, J. J., et al, supra. The probe was labeled to a specific activity of 2.0–5.0×10$^8$ cpm/µg by nick-translation, using the BRL nick-translation kit (Bethesda Research Laboratories) under recommended conditions with α [$^{32}$P] dGTP and α [$^{32}$P] dCTP (800 Ci/mmol; Amersham Corporation) in the presence of unlabeled dATP and dTTP. The probe was denatured just before the hybridization step by incubation for 5 min in a boiling water bath, followed by rapid cooling in ice water.

The apoCIII probe was a 480 bp SphI/PvuII partial cDNA fragment described in Levy-Wilson, B., et al, *DNA* (1984) 3:359–364. It was labeled similarly to the apoAI probe.

The p5′AI probe was prepared as follows: A 12.5 kb EcoRI/EcoRI fragment was isolated from a human genomic library which contains, in order, 6 kb of sequence 5′ to the apoAI gene, the entire apoAI gene, 2.6 kb of intergenic region between the apoAI and apoCIII gene, and 1.6 kb of apoCIII gene (cf. FIG. 4). This fragment was digested with HindIII and SstI and smaller fragments isolated. Most of these smaller fragments contain repetitive sequence. The 1.4 kb SsetI/-HindIII fragment resulting from this digestion contained a unique sequence appropriate as a hybridization probe and was designated p5′AI. It was labeled as described above. The p5′AI probe hybridizes close to the atherosclerosis deletion polymorphism described below, which is 4 kb 5′ of the apoAI gene. Restriction endonucleases other than XmnI could thus be used to detect this deletion, some giving fragments of smaller length which are more easily separated on agarose gel and easier to visualize.

F.2. Atherosclerosis-Associated Polymorphisms

Figure 1:
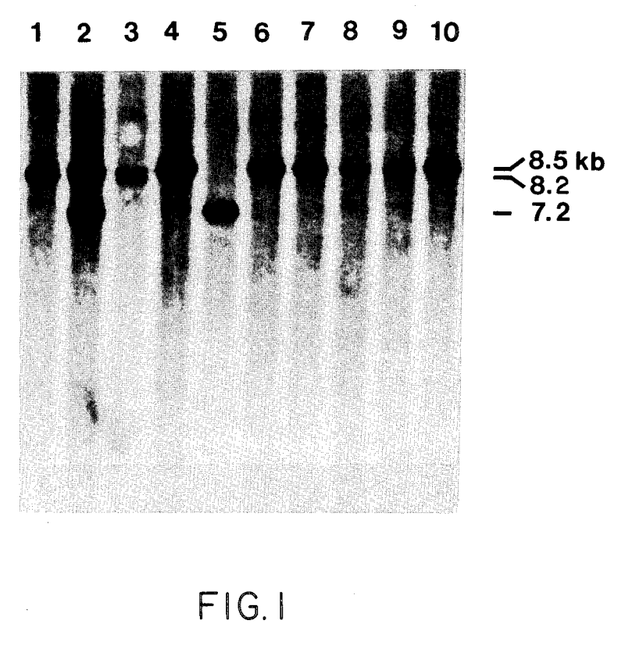
FIG. 1 shows an autoradiogram performed using XmnI-digested DNAs from 10 individuals, which have been probed by apoAI cDNA.

Using either apoAI or p5′AI as probe in the procedure of paragraph A, two polymorphisms were found when the genomic DNA was digested with XmnI. FIG. 1 shows an autoradiogram of XmnI-digested DNA from 10 individuals probed with the apoAI probe. As shown from these results, most individuals tested were homozygous and yielded only a 8.5 kb DNA fragment. One individual (lane 3) was a heterozygote of the 8.2/8.5 kb genotype, one (lane 2) was a heterozygote of the 7.2/8.5 kb genotype, and one (lane 5) was a homozygote of the 7.2 kb genotype.

The locations of these two polymorphic sites in relation to the probe sequence complementary to the apoAI gene were ascertained by treating the DNA with additional enzymes which would lead to determinative sized fragments depending on the location of the polymorphism. This strategy can best be understood with reference to FIGS. 2a and 2b which show diagrams of the relevent gene sequences along with the location of the relevant restriction sites.

Figure 2A:
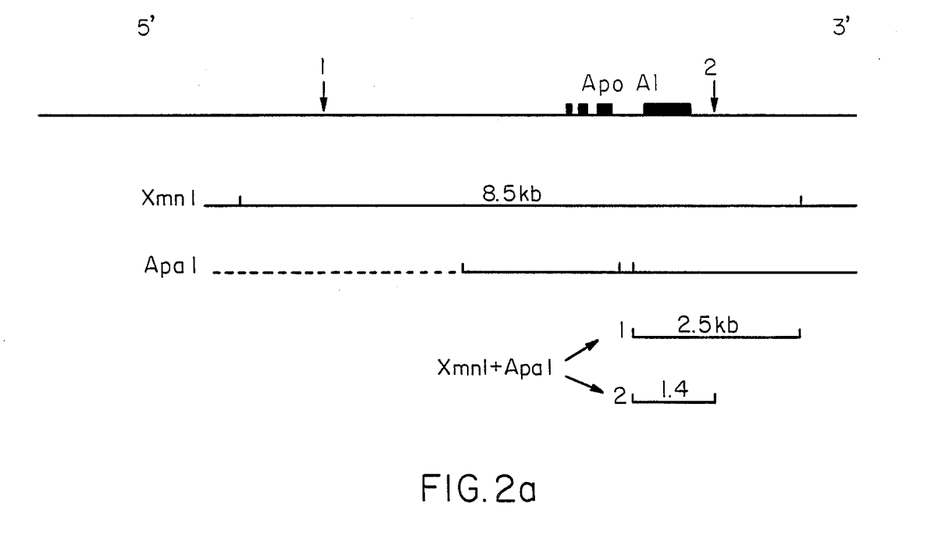
FIG. 2a shows the XmnI restriction sites in the vicinity of the apoAI gene and the putative locations of the XmnI polymorphism of the 7.2 kb type.

In FIG. 2a, the stretch of DNA which would be expected to yield to 8.5 kb fragment upon Xmn digestion is shown. Since a 7.2 kb fragment is generated in the presence of the polymorphism, there must be an additional XmnI site either at the position shown as "1→" or "2→" in the diagram. These two possibilities were distinguished by digesting DNA preparations from homozygotes with ApaI in addition to XmnI. If the additional XmnI site is at position 2, a 1.4 kb fragment is expected to result from the allele containing the polymorphism. If the new site is at position 1, only the 2.5 kb fragment associated with the "normal" sequence would be expected. When the blot hybridization experiments were performed, only the 2.5 kb fragment was found even in the individuals containing the polymorphism. Therefore, the polymorphism is located at the position of the arrow labeled 1, or approximately 3.7 kb upstream of the apoAI gene.

Figure 2B:
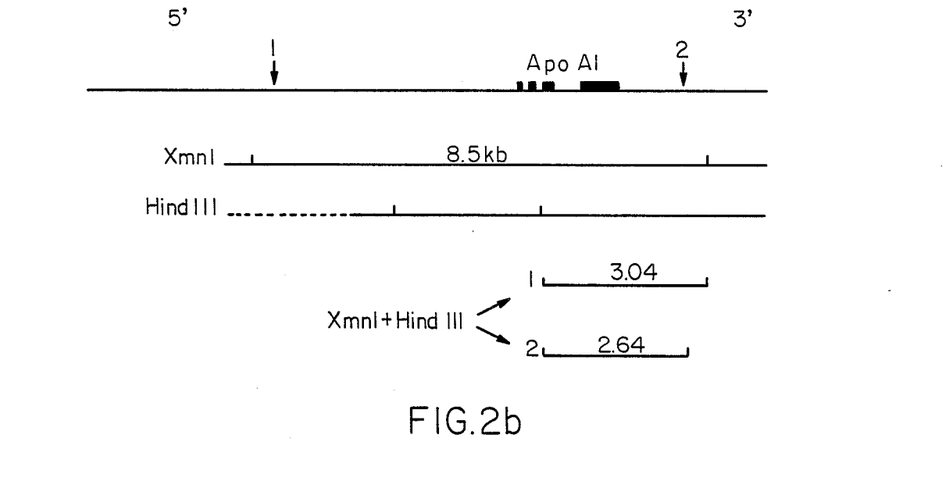
FIG. 2b shows the possible locations of the XmnI polymorphism of the 8.2 kb type.

A similar analysis with regard to the 8.2 kb fragment-yielding polymorphism is shown in FIG. 2b. The new XmnI site must be either at the position labeled "1→" or that labeled "2→". If the DNA is digested further with HindIII, polymorphisms at position 2 would lead to a 2.64 kb DNA fragment in addition to the 3.04 kb fragment expected to be generated by the normal allele. Only the normal allelic 3.04 kb fragment was found, thus leading to the conclusion that the new XmnI site is in the same position shown by the first arrow, or about 4 kb upstream from the apoAI gene. The presence of this site is generated by an approximately 300 bp deletion at this position. The frequency of this deletion was calculated to be 0.03 on the basis of 125 individuals.

Referring again to FIG. 1, lanes 1, 4, and 6–10 showed only a single band corresponding to an 8.5 kb DNA fragment. Lane 5 contained only a 7.2 kb fragment, thus representing an individual homozygous for the modification 3.7 kb 5′ of the apoAI gene. Lane 2 represents an individual heterozygous with respect to the same polymorphism, as both the 8.5 and 7.2 kb fragments are present. Lane 2 showed an individual heterozygous for the atherosclerosis deletion polymorphism, as shown by the presence of both 8.5 kb and 8.2 kb fragments.

By using the p5′AI probe, which hybridizes at a position extremely close to the location of the 300 bp 4 kb upstream deletion associated with 8.2 kb fragment formation on XmnI digestion, additional restriction enzymes could be used to detect the presence of the polymorphism. The fragments generated from the use of these enzymes are, of course, of different length from those obtained with XmnI digestion. Table 1 below shows the results obtained when DNA obtained from 5 individuals heterozygous for the atherosclerosis polymorphism were digested with series of additional enzymes and probed with p5'AI probe. The table shows the length of the fragment associated with the normal genotype, and the fragment length obtained for the polymorphism.

TABLE 1

Additional Procedures to Detect the Atherosclerosis Deletion

| Probe | Restriction Enzyme | "Normal" Fragment (kb) | "Polymorphic" Fragment (kb) |
|---|---|---|---|
| apoI or P5'AI | XmnI | 8.5 | 8.2 |
| P5'AI | ApaI | 3.5 | 3.2 |
| P5'AI | BglI | 6.2 | 5.9 |
| p5'AI | BstEII | 2.5 | 2.1 |
| p5'AI | MspI | 4.0 | 5.9 |
| p5'AI | PvuII | 1.9 | 1.6 |
| p5'AI | RsaI | 3.5 | 3.2 |
| P5'AI | StuI | 5.8 | 5.5 |
| P5'AI | TaqI | 5.2 | 9.1 |

The presence of the polymorphism which results in the generation of an 8.2 kb fragment upon XmnI digestion (or the results indicated on Table 1) correlates significantly with atherosclerosis. As described above, all individuals exhibiting this polymorphism in their genomes are not only affected by atherosclerosis but also exhibit severe clinical symptoms. However, the converse is not true: atherosclerosis may occur in individuals who lack this genetic abnormality. None of the individuals tested were homozygous with respect to this genetic feature; all contained an allele which generated the "normal" 8.5 kb fragment.

Additional polymorphisms were found which correlate in some way with the risk of atherosclerosis. To determine these polymorphisms, control and patient groups were set up using as a criterion positive or negative results relating to atheromatous plaque formation as determined by angiography. Persons were classified as "patients" who showed plaques in this assay, whether or not they had suffered heart attacks. They were designated "controls" if the results of this test were negative; none of these persons had had heart attacks.

In interpreting the results, a standard x-square analysis was used to determine a significance level. The significance level represents the probability that the results obtained would not hold up if high numbers of subjects were used. For example, a significance level of less than 0.05 means that there is a greater than 95% probability that testing additional or larger numbers of subjects would yield the same results; a significance level of 0.10 means that there is one chance in 10 that the results would be different if a larger or different sample were tested.

The findings were interpreted in terms of the relative risk of persons having the polymorphism to show the disease, compared to those having an absence of the polymorphism. These "relative incidence" values were calculated according to Wolf, B., *Ann Hum Genet* (1955) 19:251. As applied to the assays below, the relative incidence was calculated as equal to:

$$(PP \times CN)/(PN \times CP)$$

where

PP is the number of patients having the polymorphism;

PN is the number of patients not having the polymorphism;

CP is the number of controls having the polymorphism;

CN is the number of controls not having the polymorphism.

The value calculated by this ratio, if significantly greater than 1, indicates that the persons having the polymorphism are at a greater risk of having the disease; a value less than 1 shows protection against the disease.

Applying this analysis, the ApaI, XmnI/8.2, and PvuII polymorphisms correlated with an increased risk for atherosclerosis; persons having both an XmnI/7.2 and MspI polymorphism showed a significantly decreased risk. The data for each is as follows:

For the ApaI polymorphism, 90 of the 136 patients, or 66%, had the polymorphism, while 26 of 44 controls, or 59%, exhibited it. The relative risk of atherosclerosis for those with the polymorphism, as calculated above, is 1.35 times that of those without the polymorphism, with a significance value of 0.014.

For the XmnI/8.2 deletion polymorphisms, using this criterion, 16 of 113 patients, or 14%, had this polymorphism; only 4 of 44, or 9%, of controls. Applying the formula, the increased risk of the disease for those with the polymorphism is a factor of 1.7, with a significance level of 0.14.

For the PvuII polymorphism, 62 of 158 patients, or 39%, had the polymorphism; only 8 of 62 controls, or 13%. This results in an increased risk of 4.4 times for those with the polymorphism with a significance value of 0.05.

The XmnI/7.2 and MspI polymorphisms showed a relative incidence for the disease of 0.5 and 0.8, and thus appeared to be mildly protective, but with significance factors of 0.3 and 1.0, respectively. However, if the XmnI/7.2 and MspI polymorphisms are combined as halotypes, the relative incidence value is 0.25, suggesting that the individuals having both polymorphisms are four times less likely to develop atherosclerosis. This value now has a statistical significance level of 0.03. These values were based on the finding that 48 of 188, or 25%, of patients contain the XmnI/7.2 polymorphisms; 24 of 48, or 50%, of controls have it; 26 of 162, or 16%, of patients have the MspI polymorphism; 10 of 54, or 18%, of controls exhibit it.

F.3. Other Polymorphisms

Figure 3:
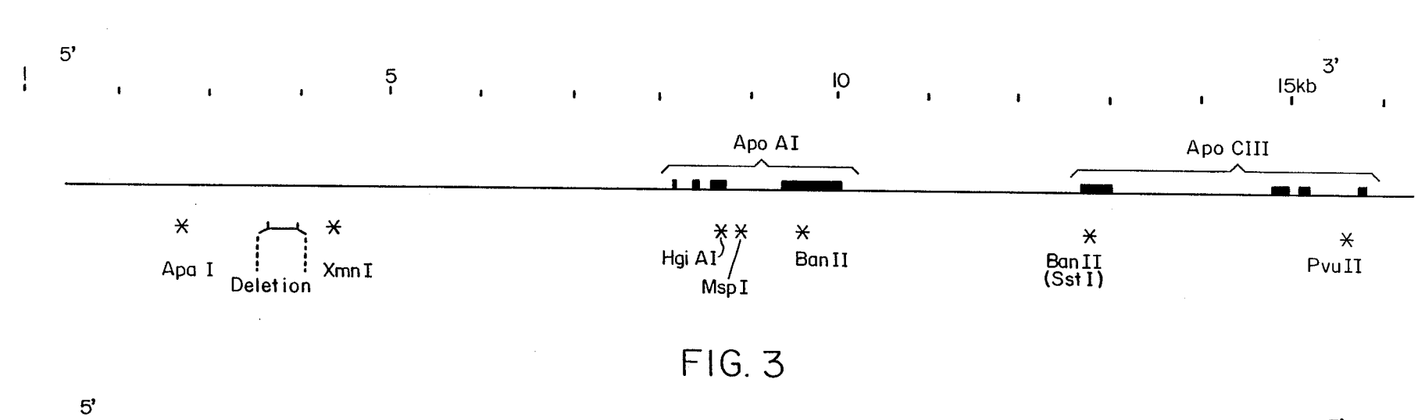
FIG. 3 shows a map of nine polymorphisms found in the apoAI/CIII gene complex.

In addition to the deletion associated with atherosclerosis and heart attack and the predictive polymorphisms for atherosclerosis outline above, a number of other polymorphisms are associated with the apoAI/CIII gene complex. The general pattern of all of these polymorphisms in the apoAI/CIII region is shown in FIG. 3 and tabulated in Table 2.

TABLE 2

| Polymorphism | Location of Polymorphism | Probe | Enzyme | "Normal" fragment | Polymorphic fragment | Freq.** |
|---|---|---|---|---|---|---|
| ApaI | 5.4 kb 5' of | p5'AI | ApaI | 3.5 | 2.2 | 0.5 |

TABLE 2-continued

| Polymorphism | Location of Polymorphism | Probe | Enzyme | "Normal" fragment | Polymorphic fragment | Freq.** |
|---|---|---|---|---|---|---|
| XmnI/8.2 | 4 kb 5' of apoAI gene | p5'AI apoAI | XmnI | 8.5 | 8.2 | 0.03 |
| XmnI/7.2 | 3.7 kb 5' of apoAI gene | p5'AI apoAI | XmnI | 8.5 | 7.2 | 0.2 |
| HgiAI | 3rd exon of apoAI gene | apoAI | HgiAI | 0.84 | 0.94 | 0.01 |
| MspI | 3rd intron of apoAI gene | apoAI | MspI | 1.08,0.67 | 1.75 | 0.12 |
| BanII | 4th exon of apoAI gene | apoAI | BanII | 0.41 | 0.47 | 0.015 |
| PstI | 0.3 kb 3' of apoAI | apoAI | PstI | 2.1 | 3.2 | 0.07 |
| *SstI/BanII | 4th exon of apoCIII gene | apoAI | SstI | 4.2 | 3.2 | 0.12 |
|  |  | apoCIII | SstI | 4.2 | 3.2,1.0 | 0.12 |
|  |  | apoCIII | BanII | 1.8 | 1.0,0.8 |  |
| PvuII | 1st intron of apoCIII gene | apoCIII | PvuII | 1.0 | 0.87 | 0.3 |

*This polymorphism as determined using apoAI probe has been shown by others and does not form part of the invention.
**Frequency is determined as follows: Each individual has two copies of each chromosome; therefore, at any locus or position on the chromosome each person has two "alleles". If these two alleles are indentical, the individual is "homozygous" at this locus; if the two alleles are different, he is heterozygous at this locus. Genetic variation between populations can be quantified using the concept of allele frequency, the proportion of all alleles in a population at he locus that are a particular allele. The frequency of any particular allele in a sample is therefore equal to twice the number of homozygotes for that allele plus the number of heterozygotes for that allele divided by two times the number of individuals in the sample.
For example, in the case of the XmnI (8.5 kb/7.2 kb) polymorphism there were:
64 homozygotes of the 8.5 kb type
6 homozygotes of the 7.2 kb type
25 heterozygotes
The polymorphic allele frequency (7.2 kb type) is thus:

$$p = \frac{25 + 2(6)}{2(64 + 6 + 25)}$$, or approximately 0.2.

(The apoAI/CIII complex was screened with a number of enzymes which do not yield polymorphisms.

Specifically, when the 600 bp partial apoAI cDNA probe was used in the procedure of paragraph A, no polymorphism was found when the DNA had been digested with any of the following enzymes: ApaI, AvaI, AvaII, BamHI, BclI, BglI, BglII, BstNI, EcoRI, EcoRV, HaeIII, HincII, HinfI, HphI, NciI, NcoI, PvuII, RsaI, ScaI, ScrFI, StuI, TaqI, and TthlII.

When the p5'Ai probe was used, no polymorphisms were obtained with AvaI, AvaII, BamHI, BanI, BanII, BclI, BglII, BstNI, EcoRI, EcoRV, HaeIII, HincIII, HinfI, HphI, NciI, PstI, ScaI, and SstI.

When apoCIII probe is used, no polymorphisms are found using AvaII, BglI, BstEII, HinfI, MspI, NcoI, RstI, RsaI, StuI, and TaqI.)

By testing a particular individual with respect to a series of polymorphisms, such as with the restriction enzymes and probes shown in Table 2, a genetic characterization (pattern) of this individual is obtained for genes associated with lipid transport. Determination of such genetic fingerprints is a tool for assigning familial relationships and heredity patterns. Such patterns are useful in determining parentage and tracing the incidence of genetic-related disorders, and in predicting the occurrence of lipid transport/metabolism disorders.

For example, in particular, 3 individuals known to be suffering from Tangier disease exhibit a haplotype (pattern of polymorphisms) which was not found in any other individual among a total 125 persons tested. This haplotype, shown below, is represented by the presence (+) or absence (−) of the indicated polymorphisms in each chromosome. The designations for the polymorphisms are those shown in Table 2.

| XmnI/8.2 | XmnI/7.2 | MspI | BanII | Sst/BanII | PvuII |
|---|---|---|---|---|---|
| +/− | −/− | −/− | −/− | −/− | −/− |

F.4. Summary of the ApoAI/CIII Polymorphisms

Figure 4:
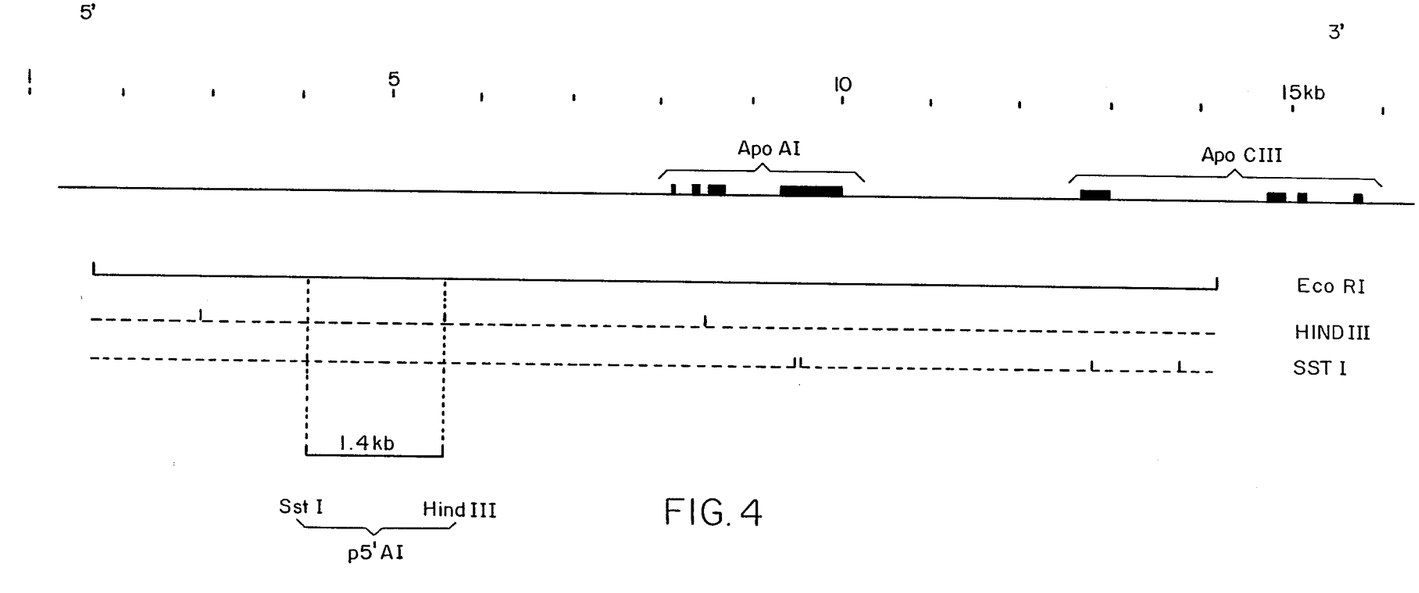
FIG. 4 shows the HindIII and SstI restriction sites in the 12.5 kb EcoRI/EcoRI fragment; and the 1.4 kb SstI/HindIII genomic probe (p5'AI) isolated to detect the 300 bp deletion associated with the 8.2 kb type.
Figure 5:
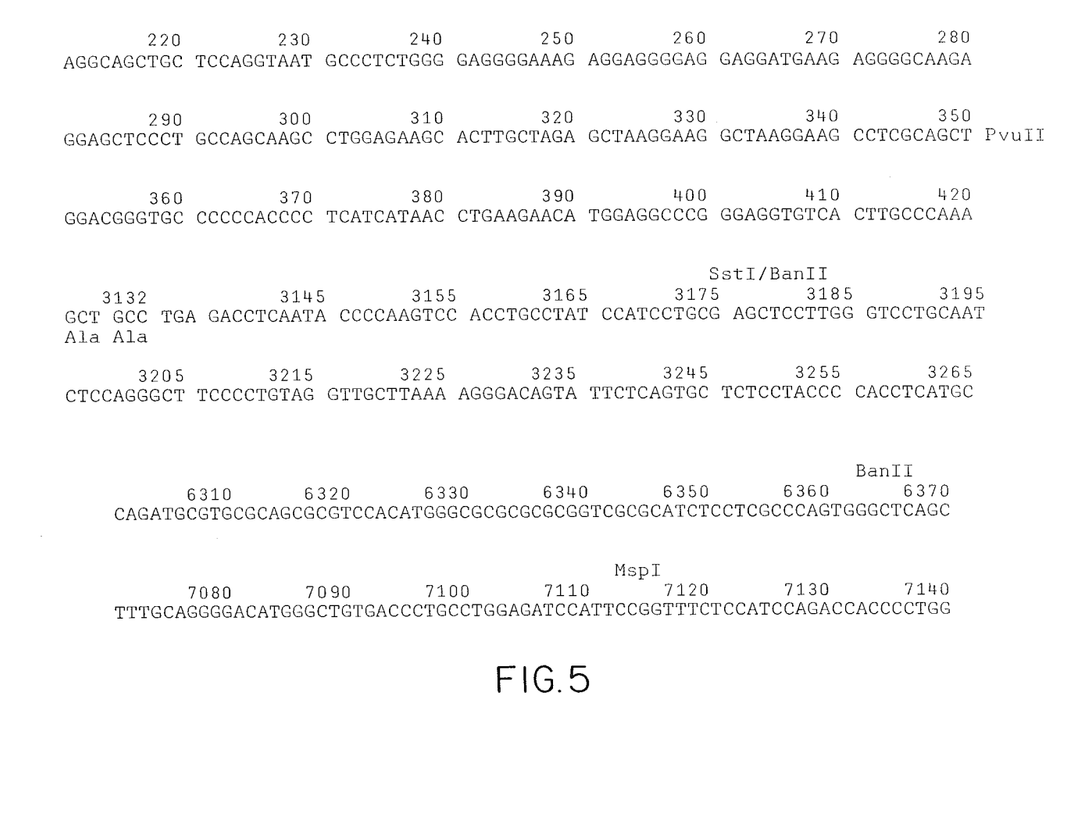
FIG. 5 shows the location of several polymorphisms in the apoAI/CIII gene region. The numbering sequence begins approximately 180 bp upstream of the 5' end of the apoCIII gene positive-sense strand and continues to the 5' end of the apoAI gene. The location and base pair changes for the PvuII, SstI/BanII, BanII and MspI polymorphisms are shown.

Table 2 summarizes nine polymorphisms of the apoAI/CIII region. Some of the listed polymorphisms have been located precisely in the sequenced portion of the apoAI/CIII gene region as shown in FIG. 5. Sequence is referenced in FIG. 5 beginning approximately 180 bp upstream of the 5' end of the apoCIII gene positive sense strand and continuing to approximately the 5' end of the apoAI gene. As shown in FIGS. 3 and 4, the apoAI and apoCIII coding sequences are read in opposite directions; therefore, the locations given in the apoAI gene by the referenced sequence are for the negative sense strand and increase in number from the downstream end of the gene.

Those locations which have been determined precisely are as shown in FIG. 5. The superscripted numbers are distances in bp from the above-indicated sequencing starting about 180 bp upstream of apoCIII. The general descriptions of the polymorphic sites are:
PvuII: G→C conversion about 160 bp from the transcription start of apoCIII;
SstI/
BanII: C→G conversion about 120 bp from the transcription termination of apoCIII;
BanII: About 360 bp from the transcription termination of apoAI.
MspI: About 750 bp from the transcription start of apoAI.

CONCLUDING REMARKS

Several of the approximately 10 million polymorphisms existent in the human genome have been shown to be useful predictors of individuals at risk for atherosclerosis. These polymorphisms are detectable as fragments of predictable size obtained by digestion of the genomic DNA of the subject individual with a specified restriction enzyme and probing with specific DNA sequences herein described. The availability of this tool for early diagnosis of individuals at risk for atherosclerosis permits the early application of therapeutic measures to prevent the fatal symptomology of the disease.

I claim:

1. A method for predicting the development of atherosclerosis in an individual human subject, which method comprises detecting the presence or absence of the "XmnI/8.2" polymorphism, which is a deletion of a 300 bp segment of DNA at 4 kb 5' of the apoAI gene.

2. The method of claim 1 which comprises detecting the presence of absence of a diagnostic length DNA fragment of human genomic DNA which has been digested with a restriction endonuclease, said fragment hybridizing to p5'AI probe, or to a substantially equivalent probe.

3. The method of claim 2 wherein the restriction endonuclease is XmnI and the length of the fragment is 8.2 kb.

4. The method of claim 2 wherein the restriction endonuclease is ApaI and the length of the restriction fragment is 3.2 kb.

5. The method of claim 2 wherein the restriction endonuclease is BglI and the length of the fragment is 5.9 kb.

6. The method of claim 2 wherein the restriction endonuclease is BstEII and the length of the fragment is 2.1 kb.

7. The method of claim 2 wherein the restriction endonuclease is MspI and the length of the fragment is 5.9 kb.

8. The method of claim 2 wherein the restriction endonuclease is PvuII and the length of the fragment is 1.6 kb.

9. The method of claim 2 wherein the restriction endonuclease is RsaI and the length of the fragment is 3.2 kb.

10. The method of claim 2 wherein the restriction endonuclease is StuI and the length of the fragment is 5.5 kb.

11. The method of claim 2 wherein the restriction endonuclease is TaqI and the length of the fragment is 9.1 kb.

12. A method for predicting the development of atherosclerosis in an individual human, which method comprises detecting the presence or absence of the "ApaI" polymorphism which is 5.4 kb 5' of the apoAI gene.

13. The method of claim 12 which comprises detecting the presence of absence of a 2.2 kb DNA fragment of human genome which has been digested with ApaI, said fragment hybridizing with p5'AI probe or a substantially equivalent probe.

14. A method for predicting the development of atherosclerosis in an individual human, which method comprises detecting the presence of absence of the "PvuII" polymorphism which is in the first intron of the apoCIII gene.

15. The method of claim 15 which comprises detecting the presence or absence of a 0.87 kb DNA fragment of human genome which has been digested with PvuII, said fragment hybridizing with apoCIII probe or a substantially equivalent probe.

16. A method for predicting decreased susceptibility to atherosclerosis in an individual human which method comprises detecting the presence or absence of the "XmnI/7.2" polymorphism which is 3.7 kb 5' of the apoAI gene and the "MspI" polymorphism which is in the third intron of the apoAI gene.

17. The method of claim 16 which comprises detecting the presence or absence of a 7.2 kb DNA fragment of human genome which has been digested with XmnI, said fragment hybridizing with apoAI or p5'AI probe or a substantially equivalent probe and a 1.75 kb DNA fragment of human genome digested with MspI, said fragment hybridizing with apoAI probe or a substantially equivalent probe.

18. A method for ascertaining individual human subjects having a propensity for disorders relating to lipid transport and metabolism, which method comprises detecting the presence or absence of one or more polymorphisms selected from the group consisting of:

the "ApaI" polymorphism 5.4 kb 5' of the apoAI gene;

the "XmnI/8.2" polymorphism 4 kb 5' of the apoAI gene;

the "XmnI/7.2" polymorphism 3.7 kb 5' of the apoAI gene in combination with the "MspI" polymorphism in the 3rd intron of the apoAI gene; and the "PvuII" polymorphism in the 1st intron of the apoCIII gene.

19. The method of claim 18 wherein each of said polymorphisms is detected in total human genomic DNA by, respectively, digestion with ApaI and detection of a 2.2 kb fragment using p5'AI probe or a substantial equivalent;

digestion with XmnI and detection of an 8.2 kb fragment using p5'AI or a substantial equivalent or apoAI or a substantial equivalent;

digestion with XmnI and detection of a 7.2 kb fragment using p5'AI or a substantial equivalent or apoAI or a substantial equivalent in combination with digestion with MspI and detection of 1.75 kb fragment using apoAI probe or a substantial equivalent; and digestion with PvuII and detection of a 0.87 kb fragment using apoCIII probe or a substantial equivalent.

20. A method of genetically identifying an individual, which method comprises assessing the presence or absence of at least one polymorphism by contacting a genomic DNA digest with apoAI probe or a substantial equivalent, wherein said digest is obtained by digesting the genome with an enzyme selected from the group consisting of XmnI, HgiAI, and PstI, or a subset thereof, and detecting the presence or absence of a diagnostic length DNA fragment which hybridizes to said probe.

21. A method of genetically identifying an individual, which method comprises assessing the presence or absence of at least one polymorphism by contacting a genomic DNA digest with p5'AI probe or a substantial equivalent, wherein said digest is obtained by digesting the genome with an enzyme selected from the group consisting of ApaI, XmnI, BglI, BstEII, PvuII, RsaI, StuI and TaqI or a subset thereof, and detecting the presence of absence of a diagnostic length DNA fragment which hybridizes to said probe.

22. A method of genetically identifying an individual which method comprises assessing the presence or absence of at least one polymorphism by
contacting a genomic DNA digest with apoCIII probe or a substantial equivalent wherein said digest is obtained by digesting the genome with BanII, PvuII or both.

23. The method of claim 2 wherein the restriction endonuclease is selected from the group consisting of XmnI, ApaI, BglI, BstEII, MspI, PvuII, RsaI, StuI, and TaqI and the length of the fragment is, respectively, 8.2 kb, 3.2 kb, 5.9 kb, 2.1 kb, 5.9 kb, 1.6 kb, 3.2 kb, 5.5 kb, 9.1 kb.

24. A method of genetically identifying an individual, which method comprises detecting the presence or absence of one or more polymorphisms selected from the group consisting of:
the "ApaI" polymorphism 5.4 kb 5' of the apoAI gene;
the "XmnI/8.2" polymorphism 4 kb 5' of the apoAI gene;
the "XmnI/7.2" polymorphism 3.7 kb 5' of the apoAI gene in combination with the "MspI" polymorphism in the 3rd intron of the apoAI gene;
the "HgiAI" polymorphism in the 3rd exon of the apoAI gene;
the "PstI" polymorphism 0.3 kb 3' of the apoAI gene; and
the "PvuII" polymorphism in the 1st intron of the apoCIII gene.

25. The method of claim 24 wherein each said polymorphism is detected in total human genomic DNA by, respectively,
digestion with ApaI and detection of a 2.2 kb fragment using p5'AI probe or a substantial equivalent;
digestion with XmnI and detection of an 8.2 kb fragment using p5'AI or a substantial equivalent or apoAI or a substantial equivalent;
digestion with XmnI and detection of a 7.2 kb fragment using p5'AI or a substantial equivalent or apoAI or a substantial equivalent in combination with digestion with MspI and detection of 1.75 kb fragment using apoAI probe or a substantial equivalent;
digestion with HgiAI and detection of 0.94 kb fragment using apoAI probe or a substantial equivalent;
digestion with PstI detection of a 3.2 kb fragment using apoAI probe or a substantial equivalent; and
digestion with PvuII and detection of a 0.87 kb fragment using apoCIII probe or a substantial equivalent.

26. A method to detect the SstI/BanII polymorphism in the 4th exon of the gene which comprises digesting the genome with BanII and detecting a 1.0 and 0.8 kb fragment using apoCIII probe or a substantial equivalent.

27. A reagent kit useful in performing the method of claim 1, which kit includes XmnI restriction enzyme and at least one probe selected from apoAI gene probe or a substantial equivalent and p5'AI probe or a substantial equivalent.

28. A reagent kit useful in performing the method of claim 1, which kit includes p5'AI probe or substantial equivalent and at least one restriction enzyme selected from the group consisting of ApaI, XmnI, BglI, BstEII, MspI, PvuII, RsaI, StuI, and TaqI.

29. A reagent kit useful in performing the method of claim 12, which kit includes ApaI restriction enzyme and p5'AI probe or a substantial equivalent.

30. A reagent kit useful in performing the method of claim 14, which kit includes PvuII restriction enzyme and apoCIII probe or a substantial equivalent.

31. A reagent kit useful in performing the method of claim 16, which kit includes XmnI restriction enzyme MspI restriction enzyme, and apoAI probe or a substantial equivalent.

32. A reagent kit useful in ascertaining individual human subjects having a propensity for disorders related to lipid transport and metabolism, which kit includes at least one probe selected from the group consisting of apoAI probe, p5'AI probe, and apoCIII probe, or their substantial equivalents, and at least one restriction enzyme selected from the group consisting of ApaI, XmnI, HgiAI, MspI, BanII, PvuII, BglI, BstEII, RsaI, StuI, and TaqI.

* * * * *